(12) United States Patent
Neifert et al.

(10) Patent No.: US 12,606,503 B2
(45) Date of Patent: Apr. 21, 2026

(54) PARAFFIN DEHYDROGENATION REACTOR ELECTRIC HEATER

(71) Applicant: LUMMUS TECHNOLOGY LLC, Houston, TX (US)

(72) Inventors: William Scott Neifert, Houston, TX (US); Sunil Panditrao, Houston, TX (US); Kandasamy Sundaram, Houston, TX (US); Gary Podrebarac, Houston, TX (US)

(73) Assignee: Lummus Technology LLC, Houston, TX (US)

( * ) Notice: Subject to any disclaimer, the term of this patent is extended or adjusted under 35 U.S.C. 154(b) by 0 days.

(21) Appl. No.: 18/486,627

(22) Filed: Oct. 13, 2023

(65) Prior Publication Data

US 2024/0124375 A1 Apr. 18, 2024

Related U.S. Application Data

(60) Provisional application No. 63/380,015, filed on Oct. 18, 2022.

(51) Int. Cl.
*C07C 5/42* (2006.01)

(52) U.S. Cl.
CPC ...................................... *C07C 5/42* (2013.01)

(58) Field of Classification Search
CPC ......... C07C 5/42; C07C 5/333; B01J 8/0446; B01J 8/0453; B01J 2208/00389;
(Continued)

(56) References Cited

U.S. PATENT DOCUMENTS 2,945,900 A * 7/1960 Douglas ................... C07C 5/48
585/443
10,017,431 B2 7/2018 Schwint et al.
(Continued)

FOREIGN PATENT DOCUMENTS

CN 104072325 A 10/2014
CN 113856571 A 12/2021
WO 2022069726 A1 4/2022

OTHER PUBLICATIONS

International Preliminary Report On Patentability issued in International Application No. PCT/US2023/035303 dated Mar. 1, 2025 (5 pages).

*Primary Examiner* — Thuan D Dang
(74) *Attorney, Agent, or Firm* — Osha Bergman Watanabe & Burton LLP

(57) ABSTRACT

A process for dehydrogenating a paraffinic feedstock, producing olefins and/or dienes. The process includes feeding a paraffinic hydrocarbon feedstock comprising one or more C2+ paraffinic hydrocarbons and a fuel gas stream to a dehydrogenation reactor preheater, combusting the fuel gas stream in the dehydrogenation reactor preheater and heating the paraffinic hydrocarbon feedstock to a temperature in the range of 500-650° C., producing a heated paraffinic feedstock, feeding the heated paraffinic feedstock to a first dehydrogenation reactor operating in a reaction mode and containing an active dehydrogenation catalyst and at least one first electrical heating element, heating the heated paraffinic feedstock in the first dehydrogenation reactor using the at least one first electrical heating element, and contacting the heated paraffinic feedstock with the active dehydrogenation catalyst and the at least one electrical heating element thereby producing an olefinic product stream comprising one or more olefins.

9 Claims, 5 Drawing Sheets

(58) Field of Classification Search
  CPC ...... B01J 2208/00407; B01J 2208/0053; B01J
                                                    8/0496
  See application file for complete search history.

(56)                    References Cited

U.S. PATENT DOCUMENTS

2002/0198428  A1 *  12/2002  Iezzi ........................ B01J 23/62
                                                      585/654
2021/0395170  A1    12/2021  Agrawal et al.
2023/0356171  A1 *  11/2023  Jenne ..................... C10G 32/02

* cited by examiner

PARAFFIN DEHYDROGENATION REACTOR ELECTRIC HEATER

FIELD OF THE DISCLOSURE

Embodiments of the present disclosure generally relate to an electrically heated furnace to produce bulk chemicals such as ethylene, propylene and butadiene as well as aromatics and other products (product gas) from a paraffinic hydrocarbon feedstock (feed gas) at large scale.

BACKGROUND

Dehydrogenation units, such as CATADIENE and CATOFIN units available from Lummus Technology LLC, dehydrogenate paraffins to olefins and olefins to dienes, and these units operate at relatively low temperatures. Hence, primary olefins (propylene from propane feed, normal butene from n-butane feed, and isobutene from isobutane feed) are the main products. When normal butenes are present in the feed, butadiene is also produced. The dehydrogenation reactions are typically carried out at low partial pressures either by operating the unit at low absolute pressure or in the presence of inert compounds, and the feed to dehydrogenation has to be heated to 500 to 650° C. to carry out the reaction to achieve economical conversions.

The energy source for heating the feedstock to dehydrogenation reactors is typically derived from burning fossil fuels with energy inputs over 900 MW for a world scale petrochemical facility. The energy input required for these facilities is very large. If this energy is supplied by burning fuel, then significant amounts of $CO_2$ are produced, which range from 0.3-1.6 tons per ton (t/t), depending on the feed to the heater.

Additionally, as the dehydrogenation reaction takes place, the dehydrogenation catalyst cools gradually and loses activity. When the catalyst is no longer capable of sustaining the dehydrogenation reaction above a desired rate, the reactor is taken out of reactor mode, and put into regeneration mode.

In regeneration mode, a regeneration air stream and a fuel gas are fed to a regeneration air heater, the fuel gas is burned, producing additional $CO_2$.

Such a dehydrogenation process consumes a lot of fuel gas in order to heat the feedstock and regenerate the catalyst.

SUMMARY OF THE DISCLOSURE

In one or more aspects, embodiments disclosed herein relate to a process for dehydrogenating a paraffinic feedstock, producing olefins and/or dienes. The process includes feeding a paraffinic hydrocarbon feedstock comprising one or more C2+ paraffinic hydrocarbons and a fuel gas stream to a dehydrogenation reactor preheater, combusting the fuel gas stream in the dehydrogenation reactor preheater and heating the paraffinic hydrocarbon feedstock to a temperature in the range of 500-600° C., producing a heated paraffinic feedstock, feeding the heated paraffinic feedstock to a first dehydrogenation reactor operating in a reaction mode and containing an active dehydrogenation catalyst and at least one first electrical heating element, heating the heated paraffinic feedstock in the first dehydrogenation reactor using the at least one first electrical heating element, and contacting the heated paraffinic feedstock with the active dehydrogenation catalyst and the at least one electrical heating element, thereby producing an olefinic product stream comprising one or more olefins.

In another aspect, embodiments disclosed herein relate to a system for dehydrogenating a paraffinic feedstock, producing olefins and/or dienes. The system includes a dehydrogenation reactor preheater for receiving a paraffinic hydrocarbon feedstock comprising one or more C2+ paraffinic hydrocarbons and a fuel gas stream, combusting the fuel gas stream, and heating the paraffinic hydrocarbon feedstock to a temperature in the range of 500-600° C., producing a heated paraffinic feedstock; and a first dehydrogenation reactor containing a catalyst bed having an active dehydrogenation catalyst and at least one first electrical heating element, the first dehydrogenation reactor configured for receiving the heated paraffinic feedstock during a reaction mode and producing an olefinic product stream comprising one or more olefins, the at least one first electrical heating element configured for heating the heated paraffinic feedstock.

Other aspects and advantages will be apparent from the following description and the appended claims.

BRIEF DESCRIPTION OF DRAWINGS

FIG. 1A illustrates a system used for production of olefins and other bulk chemicals from paraffinic hydrocarbon according to embodiments disclosed.

FIG. 1B illustrates a system for the regeneration of a catalyst for the production of olefins and other bulk chemicals from paraffinic hydrocarbons according to embodiments disclosed.

FIG. 2A illustrates a system used for production of olefins and other bulk chemicals from paraffinic hydrocarbon according to embodiments disclosed.

FIG. 2B illustrates a system for the regeneration of a catalyst for the production of olefins and other bulk chemicals from paraffinic hydrocarbons according to embodiments disclosed.

FIG. 3A illustrates a system used for production of olefins and other bulk chemicals from paraffinic hydrocarbon according to embodiments disclosed.

FIG. 3B illustrates a system for the regeneration of a catalyst for the production of olefins and other bulk chemicals from paraffinic hydrocarbons according to embodiments disclosed.

FIG. 4A illustrates a system used for production of olefins and other bulk chemicals from paraffinic hydrocarbon according to embodiments disclosed.

FIG. 4B illustrates a system for the regeneration of a catalyst for the production of olefins and other bulk chemicals from paraffinic hydrocarbons according to embodiments disclosed.

FIG. 5A illustrates a system used for production of olefins and other bulk chemicals from paraffinic hydrocarbon according to embodiments disclosed.

FIG. 5B illustrates a system for the regeneration of a catalyst for the production of olefins and other bulk chemicals from paraffinic hydrocarbons according to embodiments disclosed.

With respect to the figures, like parts are represented by like reference numerals.

DETAILED DESCRIPTION

Processes disclosed herein may be used to convert gaseous and light hydrocarbons into olefins and/or dienes. Suitable gaseous or light hydrocarbons may include ethane, propane, butanes, pentanes, and mixtures thereof. Suitably, the hydrocarbons are contained in a paraffin-containing feed including hydrocarbons having at least two carbon atoms. In some embodiments, processes disclosed herein may be used to convert ethane to ethylene, propane to propylene, and butanes to butenes, butenes to butadienes, and pentanes to pentenes and pentadienes, among other reactants and conversion products.

Hydrocarbon feedstocks that may be dehydrogenated according to embodiments herein may be a single hydrocarbon or a mixture of hydrocarbons, such as ethane, propane, butanes, butenes, pentanes, pentenes, hexanes and hexenes, among other light hydrocarbons. In some embodiments, the feed may be a mixture of hydrocarbons, such as a C2-C4 mixture, C3-C4 mixture, a C3-C5 mixture, a C4-C5 mixture, a C3-C6 mixture, or other various combinations of C3-C6 hydrocarbons. In other embodiments, the hydrocarbon feedstock may include one or more aromatic components such as ethylbenzene.

The effluent from the dehydrogenation reactor(s) may be processed to appropriately quench, compress, separate, and recover the inerts (such as methane), olefins and dienes. For example, one or more distillation towers may be used to separate the dehydrogenation reactor effluent into two or more fractions, such as a hydrogen fraction, a methane fraction, a mixed C1/C2 fraction, a mixed C2 fraction, an ethylene fraction, an ethane fraction, a C3 fraction, a propylene fraction, a propane fraction, a C4 fraction, a butadiene fraction, a butene fraction, a butane fraction, and/or a C5+ containing fraction.

The dehydrogenation processes according to embodiments herein include fixed-bed reactors that operate at low pressure and elevated temperature. Conditions are selected to optimize the complex relationship among conversion, selectivity and energy consumption in the temperature and pressure range of 400 to 750° C. and 0.01 to 1.2 bara, such as from 575-700° C. and 0.1 to 0.9 bara.

In paraffin dehydrogenation units, the endothermic heat of reaction is supplied by a combination of inputs, primarily a reactor charge heater heating the paraffin feedstock, and subjecting the reactor to a regeneration step where hot air passes over the catalyst bed, regenerating the catalyst and heating the catalyst up to a desired start-of-run reaction temperature. According to embodiments disclosed herein, the heat of reaction to the process may be supplied by a reactor charge heater, such as a fired heater, regeneration air, and one or more electric heaters embedded in the reactor. In other embodiments, the reactor charge heater or the regen air heater may also be an electrical heater, thereby allowing the dehydrogenation process to be full electric with little to no $CO_2$ emissions, other than that resulting from catalyst regeneration. In addition to reducing $CO_2$ emissions, it has been found that electric heaters embedded in the reactor may enable longer run lengths before regeneration is needed, a higher catalyst selectivity, and a reduction in greenhouse gas emissions associated with fuel firing by enabling electrification with renewable power.

Dehydrogenation is endothermic, and when the feed stream passes through the dehydrogenation catalyst, heavier molecular weight paraffins are dehydrogenated first followed by the lighter paraffins. In order to maintain conversion/selectivity of the desired amount of paraffin to the desired amount of olefin(s), heat input to the reactor remains constant. Use of an electrical heat source above, or in, the catalyst bed may add additional heat to the system without the need for co-feeding lighter hydrocarbons, such as methane, that do not react but instead add mass flow and heat transfer to the system. This additional heat input to the reactor can be balanced by reducing heat input from other sources, such as by reducing reheat air temperature anywhere from 1-50° C. at constant air flow, or reducing reheat air flowrate by 3-30% at constant air temperature, or reducing the hydrocarbon feed temperature anywhere from 1-30° C., or a combination of each. When reducing temperature at constant heat input, selectivity to the desired product(s) will be improved due to a more isothermal reactor operation at a lower temperature. Restated, supplemental heating provided by the electric heaters according to embodiments herein may reduce the peak (start) temperature required for the dehydrogenation reaction, and may result in a higher end of run temperature, overall operating more isothermal as compared to a typical adiabatic dehydrogenation reactor, both of which result in improved selectivity during a reaction cycle, as well as improving run length between catalyst regenerations. The use of ethane and/or methane as a partial pressure diluent as compared to other inert partial pressure diluents may thus inhibit the formation of undesirable heavy by-products while keeping relatively constant coke production. By doing these things in combination, the total yield to olefins may be improved in some embodiments herein.

One way to reduce or even eliminate emissions from large-scale production of olefins is electrification of the energy source, preferably where the electricity is supplied by renewable energy. Embodiments herein relate to electric heaters for the production of petrochemicals, such as ethylene, propylene, and butadiene, as well as aromatics and other products for downstream processes. More specifically, embodiments herein are directed toward electrically heated heaters to produce bulk chemicals such as ethylene, propylene and butadiene as well as aromatics and other products (product gas) from a hydrocarbon feedstock (feed gas) at large scale.

Rather than relying on burning of fossil fuels for the entirety of the required energy input, embodiments herein provide a furnace or heating element that employs electrical resistance heating. There are a number of ways to supply the electrical energy to heat the reaction feed, catalyst, or both, and provide the necessary heat flux to the hydrocarbon feed for the dehydrogenation process. These methods may include convective heating by passing a current through a heating element within catalyst bed, inductive heating by inducing an eddy current in the heating elements by surrounding the elements with an electromagnet, or radiative heating from resistive heating elements adjacent to the catalyst.

Based on the catalyst being used, the dehydrogenation feed temperature should be appropriately selected. This temperature has to be sufficient enough for carrying out the dehydrogenation reaction. Typically, this temperature (inlet to catalytic dehydrogenation reactor) is in the range from about 500° C. to about 700° C., such as in the range from about 550° C. to about 650° C. or in the range from about 500° C. to about 600° C.

Catalyst lose activity over time resulting in the need to introduce the feedstock at greater and greater temperatures. Periodically, the catalyst will need to be regenerated. During regeneration the catalyst is contacted with a regeneration gas, usually an oxygen-containing gas where remaining hydrocarbons, coke, heavy residues, and tar are removed from the catalyst. The regenerated catalyst is then contacted with an evacuation and reduction gas, resulting in in situ catalyst reduction. and the reactor with the resulting reduced catalyst is cycled back to the dehydrogenation reaction mode. The system may include a plurality of reactors such that one or more reactors are operated in reaction mode while one or more reactors may be operated in purge mode or regeneration mode, such as described in U.S. Pat. No. 10,017,431, for example.

Figures 1A, 1B:
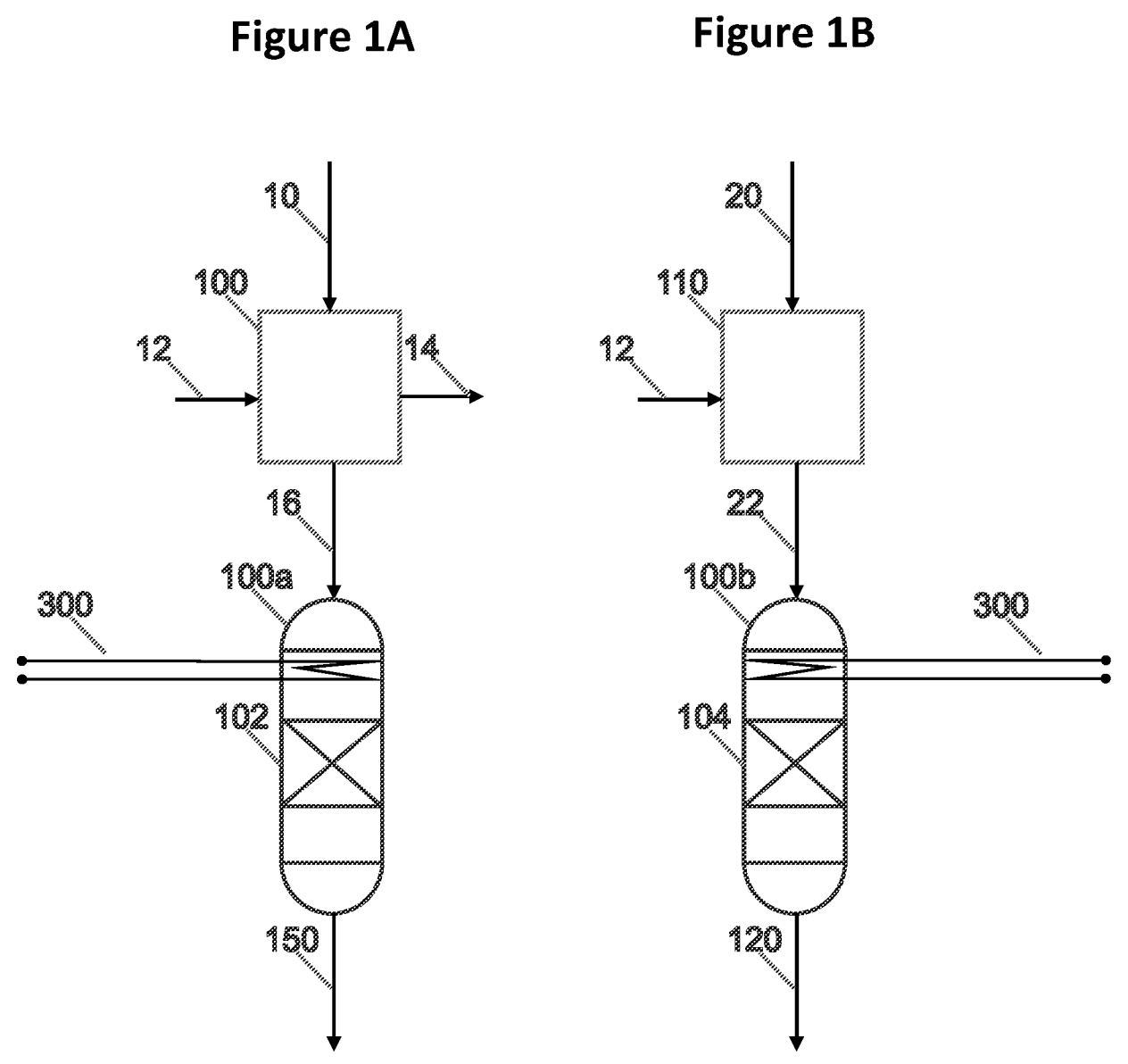

Referring now to FIGS. 1A and 1B, a simplified process diagram of a system for dehydrogenation according to embodiments herein is illustrated. As illustrated in FIG. 1A, an electrical and fuel-fired heater dehydrogenation process is illustrated. A paraffinic hydrocarbon feedstock 10 is fed to a preheater 100. A fuel gas 12, such as methane, is fed to the preheater 100 and ignited, causing an exothermic combustion reaction that preheats the paraffinic feedstock 10 to a temperature in the range of 500-650° C., such as from 500-600° C. The combustion gas 14 leaves the preheater 100 and is sent to heat recovery and flue gas stack.

The preheated feedstock 16 exits the preheater and is fed to at least one first fixed bed dehydrogenation reactor 100a. The at least one first fixed bed dehydrogenation reactor 100a is operated in reaction mode and contains an active dehydrogenation catalyst 102, and at least one first electrical heating element 300. The at least one first electrical heating element 300 may be single units, or multiple units arranged in a bundle depending on the heat requirements and mass flow of the system. The at least one first electrical heating elements 300 may provide supplemental heat duty to the feedstock. The supplemental heating may allow for a reduction in consumption of fuel gas 12, maintenance of temperature within the reactor, increased reactor run-time, or a combination thereof. The at least one first electrical heating elements 300 may also minimize residence time at higher temperatures within the reactor, which may maintain high olefin selectivity and increase heat input to the catalyst, thereby extending run length.

The preheated feedstock 16 contacts the active dehydrogenation catalyst 102, converting paraffins into olefins and producing an olefin rich reactor effluent 150 which is sent to downstream separation and storage.

The at least one first electrical heating elements 300 may be capable of 0-20 MW of heat per reactor. As noted previously, the duty may be provided in a single heating element or a group of heating elements in a bundle. For example, the at least one first electrical heating elements 300 may be in one or more rows of heating elements, such as two, or three, or four rows of heating elements. Each row of heating elements may have one or more individual heating elements, such as four individual heating elements, each providing 0-5 MW of heat. The at least one first electrical heating elements 300 may be configured to provide sensible heat to the dehydrogenation reactor to maintain a more uniform heat distribution across the reactor cross section.

The at least one first electrical heating elements 300 may be located in the dehydrogenation reactor 100a in an upper portion of the reactor, above the catalyst. The amount of electrical heating provided by the at least one first electrical heating elements 300 may vary during the course or reactor operation.

In one or more embodiments, the at least one first electrical heating elements 300 may also be used during regeneration in the at least one second fixed bed dehydrogenation reactor 100b. as illustrated in FIG. 1B. When the catalyst is no longer capable of the dehydrogenation reaction above a desired rate, the at least one first fixed bed dehydrogenation reactor 100a is taken out of reactor mode, purged with steam, and put into regeneration mode. By way of example, at least one second fixed bed dehydrogenation reactor 100b is illustrated in regeneration mode.

A regeneration air stream 20 and a fuel gas 12 are fed to a regeneration air heater 110. The regeneration air stream 20 and a fuel gas 12 mix and are ignited producing a regen air stream 22 at a temperature in the range of 600-700° C. The regen air stream 22 is fed to the at least one second fixed bed dehydrogenation reactor 100b containing a non-active dehydrogenation catalyst 104 and at least one first electrical heating elements 300. The regen air stream 22 removes coke and other material from the non-active dehydrogenation catalyst 104, thereby regenerating the catalyst and producing a flue gas 120 which is fed to heat recovery and flue gas stack (not illustrated). After the catalyst has been regenerated, an evacuation and reduction gas is fed to the at least one second fixed bed dehydrogenation reactor 100b. After the evacuation and reduction gas is fed to the at least one second fixed bed dehydrogenation reactor 100b, the at least one second fixed bed dehydrogenation reactor 100b is transferred back into reaction mode. In this manner, first fixed bed dehydrogenation reactor 100a and second fixed bed dehydrogenation reactor 100b may be cycled between reaction mode and regeneration mode.

The at least one first electrical heating elements 300 in the at least one second fixed bed dehydrogenation reactor 100b may provide additional sensible heat to the regen air stream 22, thereby improving the heat distribution in the at least one second fixed bed dehydrogenation reactor 100b.

Figures 2A, 2B:
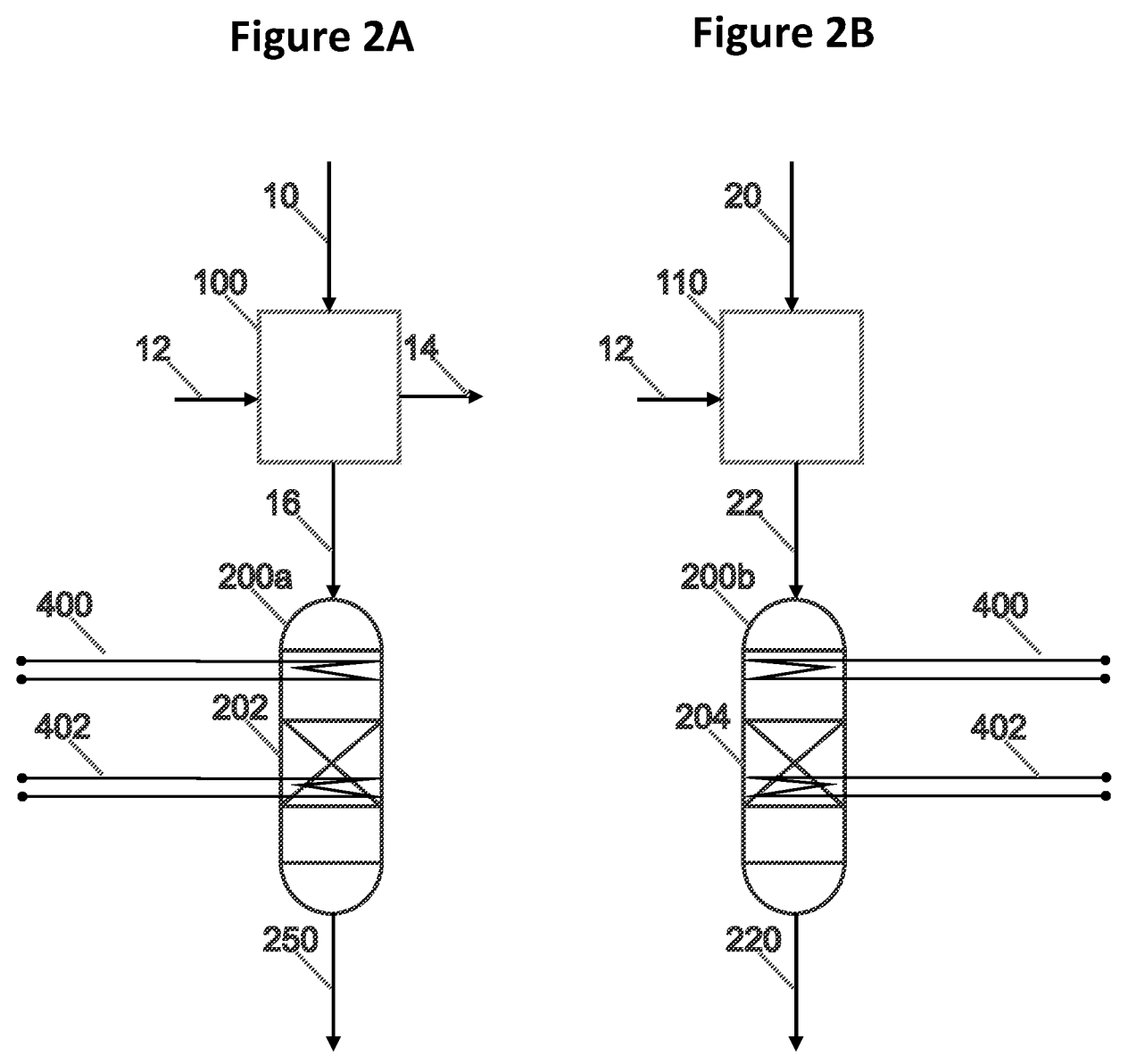

Referring now to FIGS. 2A and 2B, a simplified process diagram of a system for dehydrogenation according to embodiments herein is illustrated. As illustrated in FIG. 2A, an electrical and fuel-fired heater dehydrogenation process is illustrated. A paraffinic hydrocarbon feedstock 10 is fed to a preheater 100. A fuel gas 12, such as methane, is fed to the preheater 100a and ignited, causing an exothermic combustion reaction that preheats the paraffinic feedstock 100 to a temperature in the range of 500-600° C. The combustion gas 14 leaves the preheater 100 and is sent to heat recovery and flue gas stack.

The preheated feedstock 16 exits the preheater and is fed to at least one first fixed bed dehydrogenation reactor 200a. The at least one first fixed bed dehydrogenation reactor 200a is operated in reaction mode and contains an active dehydrogenation catalyst 202, at least one first electrical heating element 400, and at least one second electrical heating element 402. The at least one first and second electrical heating elements 400 and 402 may be single units, or multiple units arranged in a bundle depending on the heat requirements and mass flow of the system. The at least one first and second electrical heating elements 400 and 402 may provide supplemental heat duty to the feedstock. The supplemental heating may allow for a reduction in consumption of fuel gas 12, maintenance of temperature within the reactor, increased reactor run-time, or a combination thereof. The at least one first and second electrical heating elements 400 and 402 may also minimize residence time at higher temperatures within the reactor, which may maintain high olefin selectivity and increase heat input to the catalyst, thereby extending run length.

The preheated feedstock 16 contacts the active dehydrogenation catalyst 202, converting paraffins into olefins and producing an olefin rich reactor effluent 250 which is sent to downstream separation and storage.

The at least one first and second electrical heating elements 400 and 402 may be capable of 0-20 MW of heat per reactor. As noted previously, the duty may be provided in a single heating element or a group of heating elements in a bundle. For example, the at least one first and second electrical heating elements 400 and 402 may be in one or more rows of heating elements, such as two, or three, or four rows of heating elements. Each row of heating elements may have one or more individual heating elements, such as four individual heating elements, each providing 0-5 MW of heat. The at least one first and second electrical heating elements 400 and 402 may be configured to provide sensible heat to the dehydrogenation reactor to maintain a more uniform heat distribution across the reactor cross section.

Figures 3A, 3B:
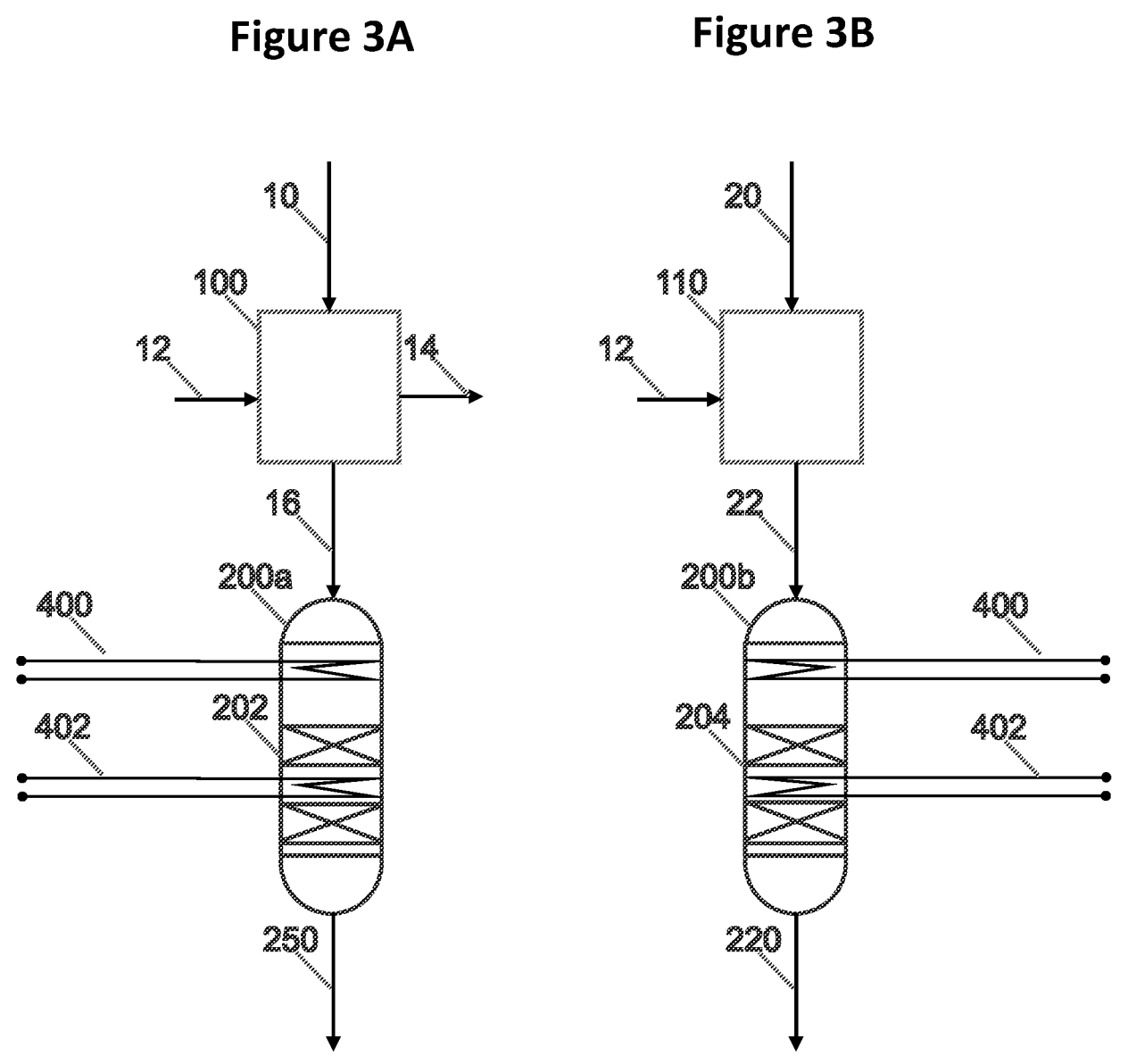
Figures 4A, 4B:
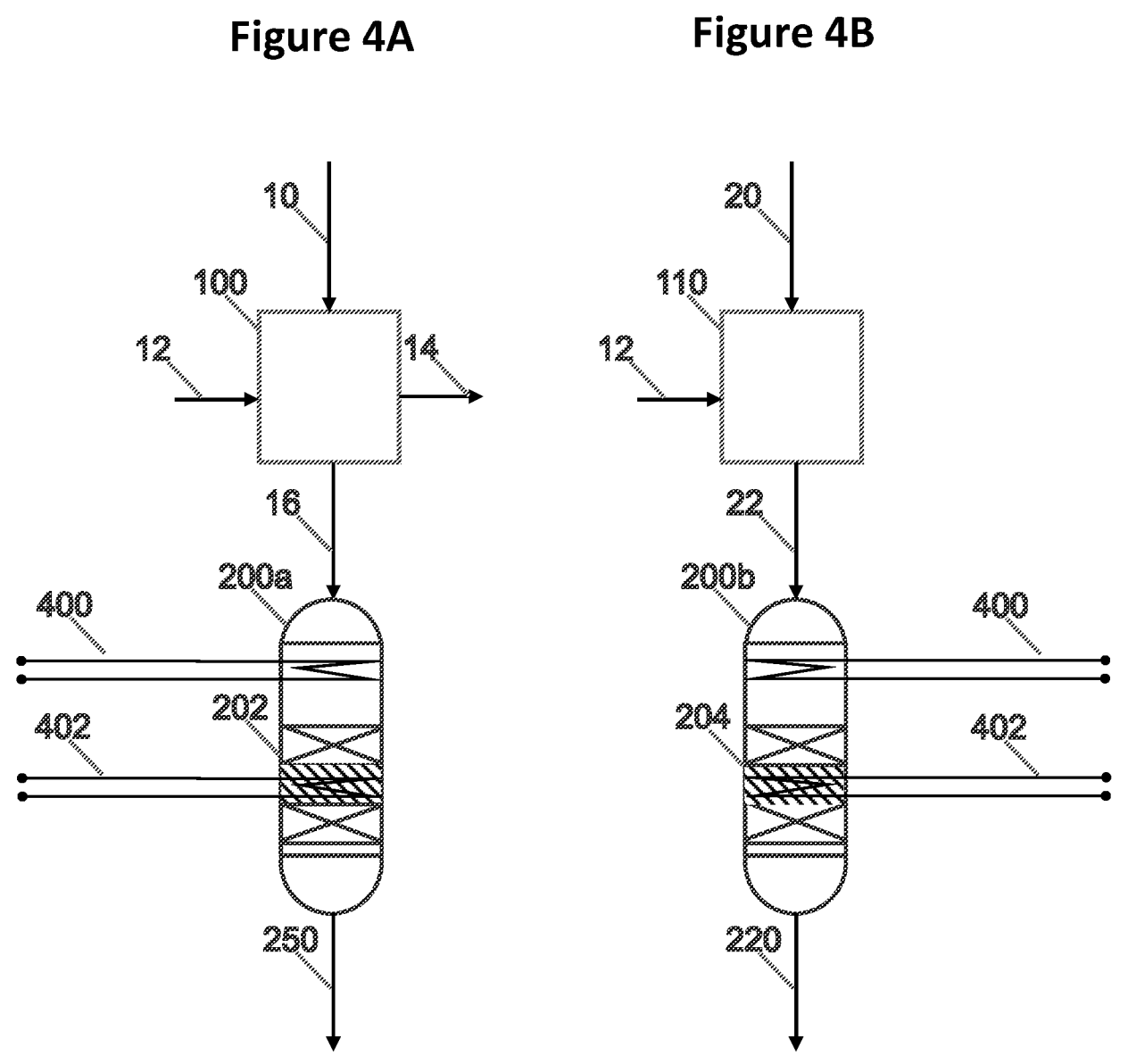
Figures 5A, 5B:
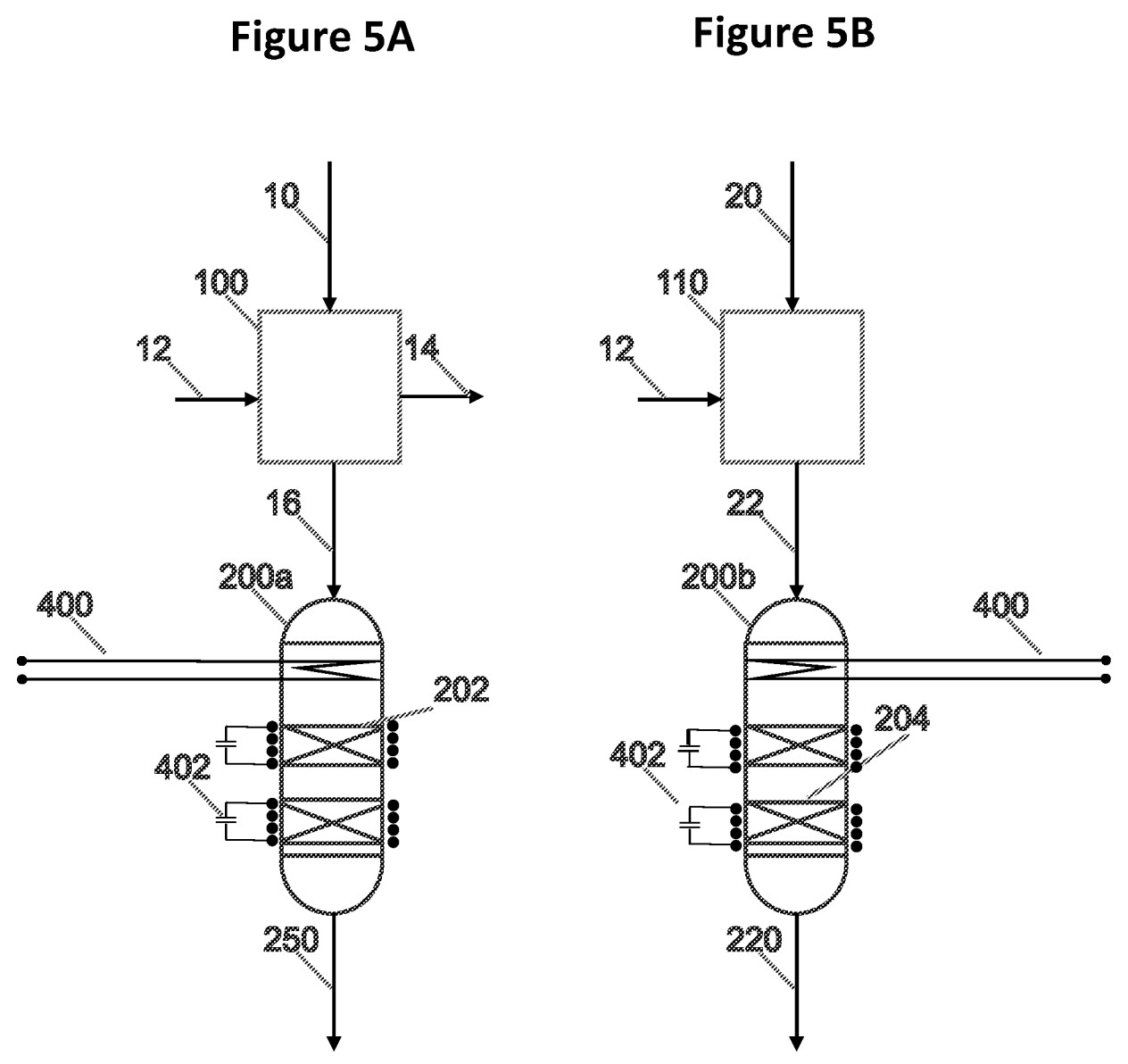

The at least one first electrical heating elements 400 may be located in the dehydrogenation reactor 200a in an upper portion of the reactor, above the catalyst. The at least one second electrical heating elements 402 may be located within the dehydrogenation catalyst 202 bed. In one or more embodiments, the at least one second electrical heating elements 402 may be located above the catalyst, intermediate upper and lower catalyst beds (FIGS. 3A and 3B), in an inert layer between the upper and lower catalyst beds filled with an inert material that conducts heat but is less conductive for electricity, such as Silicon carbide material (FIGS. 4A and 4B), or a combination thereof. Each bank of the at least one second electrical heating elements 402 may have a different number of rows, may have a different number of heating elements, may have different sizes, or may have different power limits than the at least one first electrical heating elements 400. In other embodiments, the at least one second electrical heating elements 402 may be an inductive heating element wrapped around the catalyst bed (FIGS. 5A and 5B). Such heating elements may heat the catalyst bed by inducing an eddy current in the heating elements by surrounding the heating elements with an electromagnet.

In all of the above cases the heating element may be a NiCr wire surrounded by a magnesium oxide dielectric layer and encased in a sheath of a heat resistant material such as Inconel. Alternatively, a bare wire element may be inserted into an empty tube such that heat is transferred from a glowing element to the tube wall by radiation and from the tube wall to the catalyst material and/or the flowing gas by conduction and convection heat transfer respectively.

The at least one first electrical heating elements 400 may be configured to provide sensible heat to the dehydrogenation reactor to maintain a more uniform heat distribution across the reactor cross section, while the at least one second electrical heating elements 402 may maintain the temperature of the catalyst in the catalyst bed, thereby increasing run-time. The amount of electrical heating provided by the at least one first and second electrical heating elements 400 and 402 may vary during the course or reactor operation.

In one or more embodiments, the at least one first and second electrical heating elements 400 and 402 may also be used during regeneration in the at least one second fixed bed dehydrogenation reactor 200b. When the catalyst is no longer capable of the dehydrogenation reaction above a desired rate, the at least one first fixed bed dehydrogenation reactor 200a is taken out of reactor mode, purged with steam, and put into regeneration mode. By way of example, at least one second fixed bed dehydrogenation reactor 200b is illustrated in regeneration mode.

A regeneration air stream 20 and a fuel gas 12 are fed to a regeneration air heater 110. The regeneration air stream 20 and a fuel gas 12 mix and are ignited producing a regen air stream 22 at a temperature in the range of 600-700° C. The regen air stream 22 is fed to the at least one second fixed bed dehydrogenation reactor 200b containing a non-active dehydrogenation catalyst 204 and the at least one first and second electrical heating elements 400 and 402. The regen air stream 22 removes coke and other material from the non-active dehydrogenation catalyst 204, thereby regenerating the catalyst and producing a flue gas 220 which is fed to heat recovery and flue gas stack. After the catalyst has been regenerated, an evacuation and reduction gas is fed to the at least one second fixed bed dehydrogenation reactor 200b. After the evacuation and reduction gas is fed to the at least one second fixed bed dehydrogenation reactor 200b, the at least one second fixed bed dehydrogenation reactor 200b is transferred back into reaction mode as the at least one first fixed bed dehydrogenation reactor 200a.

The at least one first electrical heating elements 400 in the at least one second fixed bed dehydrogenation reactor 200b may provide additional sensible heat to the regen air stream 22, thereby improving the heat distribution in the at least one second fixed bed dehydrogenation reactor 200b. The at least one second electrical heating elements 402 in the at least one second fixed bed dehydrogenation reactor 200b may heat the non-active catalyst 204, thereby reducing the time it takes for the catalyst to be regenerated.

The preheater is shown as a fired heater with fuel stream 12. Equivalently an electric heater can be used. Instead of full electrical heat, a hybrid heater capable of firing partly fuel and partly heated by electricity may be used. All forms of fuel and electrical heating (electrical resistance, direct heating and inductive heating) are acceptable.

Embodiments herein can use several different types of electrical heating elements. Some embodiments include a method of heating that requires resistance heating elements. Electrical heating elements of this type have limits of heat flux at high temperature. The heating elements receive an electric current at an applied voltage, and heat is generated based on the element resistance. The element will increase in temperature until the electrical energy is dissipated as heat, or the material reaches its temperature limit and fails. Hence resistance heating elements will have a limit on applied heat flux at a given temperature. As the operating temperature increases, the maximum achievable heat flux decreases.

The heating elements are supported on the reactor walls or by the catalyst bed. There are several types of heating elements that are suitable for the temperatures in the dehydrogenation reactor, including NiCr, FeCrAl, SiC and MoSi$_2$ types. NiCr is the cheapest but also the most limited with a maximum temperature of 1100° C. FeCrAl is another metallic element type that can be used up to ~1300° C. SiC elements can be applied up to 1600° C. or more, and MoSi$_2$ elements up to 1750° C. These values vary depending on the reference source but the values quoted are representative. Additionally, there is a requirement to consider aging of the elements and the appropriate operational margins. If the heating elements are operated close to their maximum permissible temperature the service life of the element may be reduced, and small increases due to changes in operation could result in element failures. Hence for the longest service life it is preferred to operate the element as far from its maximum permissible temperature as possible. In some embodiments, the heating element may be in a rod over bend (ROB) configuration or rigid Silicon Carbide rod type elements. For example, FeCrAl (metallic) elements may be provided in a rod over bend (ROB) configuration or rigid Silicon Carbide rod type elements.

In one or more embodiments, the catalyst beds may also contain a heat generating material. The heat generating material may be disposed in a plurality of tubes within the catalyst bed, or may be intermingled with the catalyst in the catalyst bed. The heat generating material may serve to maintain the heat within the catalyst bed, improving the isothermal nature of the reactor, and increasing the selectivity of the reaction as well as increase the run time. In one or more embodiments, the heat generating material may be used in conjunction with the at least one second electrical heating elements 402 to further improve the isothermal nature of the reactor and increase the selectivity of the reaction as well as increase the run time.

Benefits of embodiments disclosed herein may include reactor run lengths being extended by about 10 to 20% over the current process. For a given plant capacity, a reduction in the required amount of catalyst and reactors may be achieved, resulting in substantial CAPEX savings. Additional benefits may include increasing the selectivity of the reaction, decreasing the CO2 emissions, increasing the run length, lower the required catalyst regeneration temperature, as well as extending the time between complete catalyst replacements.

Unless defined otherwise, all technical and scientific terms used have the same meaning as commonly understood by one of ordinary skill in the art to which these systems, apparatuses, methods, processes and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed as new and desired to be protected by Letters Patent is:

1. A process for dehydrogenating a paraffinic feedstock, producing olefins and/or dienes, the process comprising:
    feeding a paraffinic hydrocarbon feedstock comprising one or more C2+ paraffinic hydrocarbons and a fuel gas stream to a dehydrogenation reactor preheater;
    combusting the fuel gas stream in the dehydrogenation reactor preheater and heating the paraffinic hydrocarbon feedstock to a temperature in the range of 500-650° C., producing a heated paraffinic feedstock;
    feeding the heated paraffinic feedstock to a first dehydrogenation reactor operating in a reaction mode and containing a catalyst bed having an active dehydrogenation catalyst and at least one first electrical heating element disposed within the first dehydrogenation reactor above or in the catalyst bed;
    heating the heated paraffinic feedstock in the first dehydrogenation reactor using the at least one first electrical heating element;
    contacting the heated paraffinic feedstock with the active dehydrogenation catalyst and the at least one electrical heating element, producing an olefinic product stream comprising one or more olefins.

2. The process of claim 1, further comprising switching the first dehydrogenation reactor operating in the reaction mode to a regeneration mode.

3. The process of claim 2, further comprising regenerating a non-active dehydrogenation catalyst in the first dehydrogenation reactor operating in the regeneration mode.

4. The process of claim 3, further comprising:
    feeding a regeneration air stream and a second fuel gas stream to a regeneration air heater;
    combusting the regeneration air stream and the second fuel gas stream in the regeneration air heater, producing a regen air stream having a temperature in the range of 600-700° C.;
    feeding the regen air stream to the first dehydrogenation reactor operating in the regeneration mode and containing the non-active dehydrogenation catalyst and at least one electrical heating element;
    contacting the regen air stream with the non-active dehydrogenation catalyst and the at least one electrical heating element, thereby regenerating the non-active dehydrogenation catalyst.

5. The process of claim 4, further comprising switching the first dehydrogenation reactor from the regeneration mode to the reaction mode.

6. The process of claim 5, further comprising heating the heated paraffinic feedstock in the first dehydrogenation reactor using at least one second electrical heating element.

7. The process of claim 6, further comprising heating the active dehydrogenation catalyst in the first dehydrogenation reactor using the at least one second electrical heating element.

8. The process of claim 7, further comprising heating the regen air stream in the first dehydrogenation reactor using the at least one first electrical heating element.

9. The process of claim 8, further comprising heating the non-active dehydrogenation catalyst in the first dehydrogenation reactor using the at least one second electrical heating element.

* * * * *